(12) United States Patent
Colice et al.

(10) Patent No.: US 9,173,572 B2
(45) Date of Patent: Nov. 3, 2015

(54) SYSTEM, METHOD AND COMPUTER-ACCESSIBLE MEDIUM FOR TRACKING VESSEL MOTION DURING THREE-DIMENSIONAL CORONARY ARTERY MICROSCOPY

(71) Applicant: THE GENERAL HOSPITAL CORPORATION, Boston, MA (US)

(72) Inventors: Christopher Max Colice, Boston, MA (US); Brett Eugene Bouma, Quincy, MA (US); Guillermo J. Tearney, Cambridge, MA (US); Jinyong Ha, Cambridge, MA (US); Milen Shishkov, Watertown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/088,906

(22) Filed: Nov. 25, 2013

(65) Prior Publication Data
US 2014/0206989 A1 Jul. 24, 2014

Related U.S. Application Data

(63) Continuation of application No. 12/437,392, filed on May 7, 2009, now Pat. No. 8,593,619.

(60) Provisional application No. 61/051,231, filed on May 7, 2008.

(51) Int. Cl.
*A61B 5/00* (2006.01)
*A61B 5/11* (2006.01)
(Continued)

(52) U.S. Cl.
CPC .............. *A61B 5/0084* (2013.01); *A61B 5/0062* (2013.01); *A61B 5/0066* (2013.01);
(Continued)

(58) Field of Classification Search
CPC ........... G01S 17/58; G01S 17/00; G01P 3/36; G01P 3/366
USPC ........................................................... 356/28
See application file for complete search history.

(56) References Cited

U.S. PATENT DOCUMENTS

| 2,339,754 A | 1/1944 | Brace |
| 3,090,753 A | 5/1963 | Matuszak et al. |

(Continued)

FOREIGN PATENT DOCUMENTS

| CA | 1550203 | 12/2004 |
| JP | 20040056907 | 2/1992 |

(Continued)

OTHER PUBLICATIONS

International Search Report for International Patent Application No. PCT/US2009/043178 mailed on Dec. 2, 2009.

(Continued)

*Primary Examiner* — Luke Ratcliffe
(74) *Attorney, Agent, or Firm* — Andrews Kurth LLP

(57) ABSTRACT

Exemplary embodiments of apparatus, method and computer accessible medium can be provided which can facilitate a determination of at least one characteristic of a structure. For example, it is possible to use at least one first arrangement which can be structured to provide at least one first transmitted radiation along a first axis and at least one second transmitted radiation along a second axis. The first and second transmitted radiations can impact the structure and generate respective first and second returned radiation. The first and second axis can be provided at a predetermined angle with respect with one another which is greater than 0. Further, at least one second arrangement can be provided which can be configured to receive data associated with the first and second returned radiations, and determine at least one relative velocity between the structure and the first arrangement along the first and second axes.

12 Claims, 5 Drawing Sheets

(51) Int. Cl.

| | | |
|---|---|---|
| *A61B 8/12* | (2006.01) | |
| *A61B 19/00* | (2006.01) | |
| *G01S 15/50* | (2006.01) | |
| *G01S 15/87* | (2006.01) | |
| *G01S 17/50* | (2006.01) | |
| *G01S 17/87* | (2006.01) | |
| *A61B 8/08* | (2006.01) | |
| *A61B 5/107* | (2006.01) | |
| *G01S 15/60* | (2006.01) | |

(52) U.S. Cl.
CPC .............. *A61B5/1114* (2013.01); *A61B 5/489* (2013.01); *A61B 8/08* (2013.01); *A61B 8/0891* (2013.01); *A61B 8/12* (2013.01); *A61B 8/488* (2013.01); *A61B 19/52* (2013.01); *G01S 15/50* (2013.01); *G01S 15/87* (2013.01); *G01S 17/50* (2013.01); *G01S 17/87* (2013.01); *A61B 5/0097* (2013.01); *A61B 5/1076* (2013.01); *A61B 5/6844* (2013.01); *A61B 5/6852* (2013.01); *A61B 2019/5278* (2013.01); *A61B 2019/5289* (2013.01); *G01S 15/60* (2013.01)

(56) References Cited

U.S. PATENT DOCUMENTS

| | | |
|---|---|---|
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,470,696 A * | 9/1984 | Ballard ........................ 356/28.5 |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefèvre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,197,470 A | 3/1993 | Helfer et al. |
| 5,202,745 A | 4/1993 | Sorin et al. |
| 5,202,931 A | 4/1993 | Bacus |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,251,009 A | 10/1993 | Bruno |
| 5,262,644 A | 11/1993 | Maguire |
| 5,275,594 A | 1/1994 | Baker et al. |
| 5,281,811 A | 1/1994 | Lewis |
| 5,283,795 A | 2/1994 | Fink |
| 5,291,885 A | 3/1994 | Taniji et al. |
| 5,293,872 A | 3/1994 | Alfano et al. |
| 5,293,873 A | 3/1994 | Fang |
| 5,302,025 A | 4/1994 | Kleinerman |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,400,771 A | 3/1995 | Pirak et al. |
| 5,404,415 A | 4/1995 | Mori et al. |
| 5,411,016 A | 5/1995 | Kume et al. |
| 5,414,509 A | 5/1995 | Veligdan |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,479,928 A | 1/1996 | Cathignol et al. |
| 5,486,701 A | 1/1996 | Norton et al. |
| 5,491,524 A | 2/1996 | Hellmuth et al. |
| 5,491,552 A | 2/1996 | Knuttel |
| 5,522,004 A | 5/1996 | Djupsjobacka et al. |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knuttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab |
| 5,635,830 A | 6/1997 | Itoh |
| 5,649,924 A | 7/1997 | Everett et al. |
| 5,697,373 A | 12/1997 | Richards-Kortum et al. |
| 5,698,397 A | 12/1997 | Zarling et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |

(56) References Cited

U.S. PATENT DOCUMENTS

| | | |
|---|---|---|
| 5,752,518 A | 5/1998 | McGee et al. |
| 5,784,352 A | 7/1998 | Swanson et al. |
| 5,785,651 A | 7/1998 | Baker et al. |
| 5,795,295 A | 8/1998 | Hellmuth et al. |
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,810,719 A | 9/1998 | Toida |
| 5,817,144 A | 10/1998 | Gregory |
| 5,836,877 A | 11/1998 | Zavislan |
| 5,840,023 A | 11/1998 | Oraevsky et al. |
| 5,840,031 A | 11/1998 | Crowley |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | Harris et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,989,191 A | 11/1999 | Scampini |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | Dimarzio |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochmann et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,268 B1 | 8/2001 | Miller et al. |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang et al. |
| 6,564,087 B1 | 5/2003 | Pitris et al. |
| 6,564,089 B2 | 5/2003 | Izatt et al. |
| 6,567,585 B2 | 5/2003 | Harris |
| 6,593,101 B2 | 7/2003 | Richards-Kortum et al. |
| 6,611,833 B1 | 8/2003 | Johnson |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |

(56) References Cited

U.S. PATENT DOCUMENTS

| | | |
|---|---|---|
| 6,725,073 B1 | 4/2004 | Motamedi et al. |
| 6,738,144 B1 | 5/2004 | Dogariu |
| 6,741,355 B2 | 5/2004 | Drabarek |
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Guillermo et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,365,858 B2 | 4/2008 | Fang-Yen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,805,034 B2 | 9/2010 | Kato et al. |
| 7,911,621 B2 | 3/2011 | Motaghiannezam et al. |
| 7,969,578 B2 | 6/2011 | Yun et al. |
| 7,973,936 B2 | 7/2011 | Dantus |
| 2001/0020126 A1 | 9/2001 | Swanson et al. |
| 2001/0036002 A1 | 11/2001 | Tearney et al. |
| 2001/0047137 A1 | 11/2001 | Moreno et al. |
| 2002/0016533 A1 | 2/2002 | Marchitto et al. |
| 2002/0024015 A1 | 2/2002 | Hoffmann et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Roche et al. |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |
| 2002/0166946 A1 | 11/2002 | Iizuka et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0191392 A1 | 10/2003 | Haldeman |
| 2003/0199769 A1 | 10/2003 | Podoleanu et al. |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039252 A1 | 2/2004 | Koch |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0189999 A1 | 9/2004 | De Groot et al. |
| 2004/0212808 A1 | 10/2004 | Okawa et al. |
| 2004/0239938 A1 | 12/2004 | Izatt |
| 2004/0246490 A1 | 12/2004 | Wang |
| 2004/0246583 A1 | 12/2004 | Mueller et al. |
| 2004/0247268 A1 | 12/2004 | Ishihara et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0004453 A1 | 1/2005 | Tearney et al. |

(56) References Cited

U.S. PATENT DOCUMENTS

| | | |
|---|---|---|
| 2005/0018133 A1 | 1/2005 | Huang et al. |
| 2005/0018200 A1 | 1/2005 | Guillermo et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu |
| 2005/0197530 A1 | 9/2005 | Wallace et al. |
| 2005/0221270 A1 | 10/2005 | Connelly et al. |
| 2005/0254061 A1 | 11/2005 | Alphonse |
| 2006/0020172 A1 | 1/2006 | Luerssen et al. |
| 2006/0033923 A1 | 2/2006 | Hirasawa et al. |
| 2006/0039004 A1 | 2/2006 | De Boer et al. |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0167363 A1 | 7/2006 | Bernstein et al. |
| 2006/0171503 A1 | 8/2006 | O'Hara et al. |
| 2006/0184048 A1 | 8/2006 | Saadat et al. |
| 2006/0193352 A1 | 8/2006 | Chong et al. |
| 2006/0224053 A1* | 10/2006 | Black et al. .............. 600/310 |
| 2006/0244973 A1 | 11/2006 | Yun et al. |
| 2006/0279742 A1 | 12/2006 | Tearney et al. |
| 2007/0002435 A1 | 1/2007 | Ye et al. |
| 2007/0019208 A1 | 1/2007 | Toida et al. |
| 2007/0038040 A1 | 2/2007 | Cense et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Milan et al. |
| 2007/0203404 A1 | 8/2007 | Zysk et al. |
| 2007/0208225 A1 | 9/2007 | Czaniera et al. |
| 2007/0223006 A1 | 9/2007 | Tearney et al. |
| 2007/0233056 A1 | 10/2007 | Yun |
| 2007/0233396 A1 | 10/2007 | Tearney et al. |
| 2007/0236700 A1 | 10/2007 | Yun et al. |
| 2007/0258094 A1 | 11/2007 | Izatt et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0013960 A1 | 1/2008 | Tearney et al. |
| 2008/0021275 A1 | 1/2008 | Tearney et al. |
| 2008/0049220 A1 | 2/2008 | Izzia et al. |
| 2008/0070323 A1 | 3/2008 | Hess et al. |
| 2008/0094613 A1 | 4/2008 | de Boer et al. |
| 2008/0094637 A1 | 4/2008 | de Boer et al. |
| 2008/0097225 A1 | 4/2008 | Tearney et al. |
| 2008/0097709 A1 | 4/2008 | de Boer et al. |
| 2008/0100837 A1 | 5/2008 | de Boer et al. |
| 2008/0139906 A1 | 6/2008 | Bussek |
| 2008/0152353 A1 | 6/2008 | de Boer et al. |
| 2008/0154090 A1 | 6/2008 | Hashimshony |
| 2008/0192236 A1 | 8/2008 | Smith et al. |
| 2008/0204762 A1 | 8/2008 | Izatt et al. |
| 2008/0218696 A1 | 9/2008 | Mir |
| 2008/0228086 A1 | 9/2008 | Ilegbusi et al. |
| 2008/0234560 A1 | 9/2008 | Nomoto et al. |
| 2008/0265130 A1 | 10/2008 | Colomb et al. |
| 2008/0308730 A1 | 12/2008 | Vizi et al. |
| 2009/0005691 A1 | 1/2009 | Huang et al. |
| 2009/0011948 A1 | 1/2009 | Uniu et al. |
| 2009/0044799 A1 | 2/2009 | Qiu |
| 2009/0051923 A1 | 2/2009 | Zuluaga |
| 2009/0131801 A1 | 5/2009 | Suter et al. |
| 2009/0192358 A1 | 7/2009 | Jaffer et al. |
| 2009/0196477 A1 | 8/2009 | Cense et al. |
| 2009/0209834 A1 | 8/2009 | Fine |
| 2009/0273777 A1 | 11/2009 | Yun et al. |
| 2009/0281390 A1 | 11/2009 | Qiu et al. |
| 2009/0290156 A1 | 11/2009 | Popescu et al. |
| 2009/0305309 A1 | 12/2009 | Chien et al. |
| 2009/0323056 A1 | 12/2009 | Yun et al. |
| 2010/0002241 A1 | 1/2010 | Hirose |
| 2010/0086251 A1 | 4/2010 | Xu et al. |
| 2010/0094576 A1 | 4/2010 | De Boer et al. |
| 2010/0150467 A1 | 6/2010 | Zhao et al. |
| 2010/0261995 A1 | 10/2010 | Mckenna et al. |

FOREIGN PATENT DOCUMENTS

| | | |
|---|---|---|
| JP | 2002-148185 | 5/2002 |
| JP | 20030035659 | 2/2003 |
| JP | 2003-102672 | 4/2012 |
| WO | 0237075 | 5/2002 |
| WO | 03013624 | 2/2003 |
| WO | 03053226 | 7/2003 |
| WO | 20050082225 | 9/2005 |
| WO | 2006038876 | 4/2006 |

OTHER PUBLICATIONS

International Written Opinion for International Patent Application No. PCT/US2009/043178 mailed on Dec. 2, 2009.

The extended European Search Report for European Patent Application No. 09 743 687.7 dated Jul. 26, 2013.

The European Communication Pursuant to Article 94(3) Patent Application No. 09 743 687.7 dated Apr. 22, 2014.

The First Office Action for Japanese Patent Application No. 2011-508674 mailed on May 7, 2013.

The Second Office Action for Japanese Patent Application No. 2011-508674 mailed on Feb. 18, 2014.

Seok H. Yun et al., "Comprehensive volumetric optical microscopy in vivo", Nature Medicine, vol. 12, No. 12, pp. 1429-1433, (2007).

European Communication Pursuant to Article 94(3) Patent Application No. 09 743 687.7 dated Jul. 16, 2014.

* cited by examiner

SYSTEM, METHOD AND COMPUTER-ACCESSIBLE MEDIUM FOR TRACKING VESSEL MOTION DURING THREE-DIMENSIONAL CORONARY ARTERY MICROSCOPY

CROSS-REFERENCE TO RELATED APPLICATION(S)

This application is a continuation of U.S. patent application Ser. No. 12/437,392 filed on May 7, 2009, which claims the benefit of priority from U.S. Patent Application No. 61/051,231, filed on May 7, 2008, the entire disclosures of which are incorporated herein by reference.

FIELD OF THE DISCLOSURE

The present disclosure relates to exemplary embodiments of systems, methods and computer-accessible medium for monitoring of relative spatial locations or motions between an instrument and a sample, and more particularly to exemplary embodiments of systems, methods and computer-accessible medium for tracking vessel motion during, e.g., a three-dimensional coronary artery microscopy procedure.

BACKGROUND INFORMATION

In certain applications, it can be desirable to monitor the relative location or motion between two objects. For example, in certain applications, it can be beneficial to precisely direct a well-defined beam or sensing vector along particular directions or at specific locations with respect to a sample. It can therefore be important to provide knowledge about the relative location or motion between the beam or sensing vector and the sample. In several laser procedures, for example, it can be desirable to scan a laser beam across a sample according to a predetermined scan pattern or at specific locations. In cases where the sample may undergo uncontrolled motion, the precision with which the predetermined scan pattern or specific location can be achieved can be compromised. In certain sensing or imaging applications, it can be important to control the sensing point or axis with respect to a sample. In order to generate two- or three-dimensional images, the sensing point or axis can be scanned with respect to the sample according to a predetermined pattern. For accurate imaging reproduction of the structure of the sample, it can be important that the predetermined scan pattern is precisely followed. In the presence of uncontrolled sample motion, the actual scan pattern on or within the sample can differ from the predetermined scan pattern and image fidelity can be compromised.

One general category of strategies that can be commonly followed for monitoring the spatial location or motion between two objects is to monitor the location or motion of each objects with respect to a known or controlled reference point. This type of strategy can be relevant in cases where one object and the reference point are persistently located with respect to one another. In medical catheter-based imaging applications, for example, the signal transducer can be placed at the distal end of a catheter, which can be inserted within an animal or human body. The transducer can be connected to an actuator at a proximal end of the catheter using an axially non-extensible, torque-conveying element such that as the actuator rotates or pushes or pulls the element, the actuator's motion is replicated accurately at the transducer. When the tissue or organ that is being imaged is not moving, and further, when the imaging system is not moving, then the constraint that one object and the reference point can be fixed with respect to one another is met. Therefore, the relative location and/or motion of the transducer with respect to the organ or tissue can be monitored and controlled. In some cases, however, the organ or tissue may undergo motion, e.g., due to respiration, cardiac function, peristalsis or patient motion, and this general category of strategy may not be applicable. Further, motion within the body, along the length of the catheter, can result in an uncontrolled motion of a distal end and of the transducer of the catheter with respect to the tissue of interest.

In certain medical procedures, it can be preferable to monitor the location and/or motion of an instrument with respect to a specific anatomical location or organ. An exemplary strategy to accomplish this objective can be to prepare the instrument so that it can be detected by an imaging modality that also facilitates a detection of the specific anatomical location or organ. In certain cases, however, the anatomical location or organ may not exhibit sufficient contrast for detection. For example, by fluoroscopy or X-ray computed tomography, the soft-tissues of the body can exhibit low relative contrast. For example, coronary arteries may not, therefore, be located with these techniques without the use of exogenous contrast agents. Furthermore, certain conventional imaging technologies may not have a sufficient resolution to precisely determine the relative location or motion of an instrument with respect to a specific anatomical location or organ.

The above-described issues and deficiencies are merely representative of a need for more precisely monitoring the relative location or motion between two objects. Indeed, it may be beneficial to address and/or overcome at least some of the deficiencies described herein above.

SUMMARY OF THE INVENTION

In order to overcome at least some of the deficiencies described above, exemplary embodiments according to the present disclosure can be provided for accurately monitoring the relative location and/or motion between two objects. In one exemplary embodiment, one object can be configured to emit an acoustic or electromagnetic radiation, which may be scattered by the second object. The first object can be further configured to collect at least a portion of the scattered acoustic or electromagnetic radiation and process this signal to determine the relative distance and/or relative velocity between the two objects. In another exemplary embodiment of the present disclosure, the first object can be facilitated to provide two or more distinct acoustic or electromagnetic radiations, which can be directed along distinct propagation axes having predetermined angles with respect to one another, and which can further scatter from the second object. In this embodiment, the first object may be further configured to collect two or more of the scattered acoustic or electromagnetic radiations and to process the corresponding signals in order to determine the relative motion of the two objects in two or more spatial dimensions.

According to still another exemplary embodiment of the present disclosure, a medical catheter can be provided which is configured to deliver at least one beam of light that may be reflected by a specific anatomical location or biological organ. The exemplary catheter can be further configured to detect the reflected light and to process this signal to determine the relative distance and/or relative velocity between the catheter and the biological site. Exemplary embodiments of methods for processing the signal can be based on the Doppler frequency shift imparted on the reflected light by the motion of the second object. By tracking the relative velocity over time, the distance between the two objects may be monitored. The medical catheter can be further configured to deliver multiple light beams, having distinct wavelength components and directed through distinct spatial angles with respect to one another so that the relative velocity vector between the catheter and the specific anatomical site or biological organ can be determined.

Thus, according to certain exemplary embodiments of the present disclosure, apparatus, method and computer accessible medium can be provided which can facilitate a determination of at least one characteristic of a structure. For example, it is possible to use at least one first arrangement which can be structured to provide at least one first transmitted radiation along a first axis and at least one second transmitted radiation along a second axis. The first and second transmitted radiations can impact the structure and generate respective first and second returned radiation. The first and second axis can be provided at a predetermined angle with respect with one another which is greater than 0. Further, at least one second arrangement can be provided which can be configured to receive data associated with the first and second returned radiations, and determine at least one relative velocity between the structure and the first arrangement along the first and second axes.

In another exemplary embodiment of the present disclosure, the first and second transmitted radiations can be electro-magnetic radiations and/or ultrasound radiations. Further, the first and second transmitted radiations can have different wavelengths. In addition, the data can correspond to a Doppler shift between the first and second transmitted radiations and the first and second returned radiations. The data can also correspond to, e.g., a time rate of change of a distance between the apparatus and the structure along the first and second axes.

According to still another exemplary embodiment of the present disclosure, the first arrangement can extend along a longitudinal axis, and a first velocity along the first axis and a second velocity along the second axis can be used to determine a further relative velocity between the apparatus and the structure at least approximately along the longitudinal axis. In addition, a position and/or a rotation of the apparatus can be determined based on the further relative velocity. Further, at least one third arrangement which can be configured to generate at least one image of at least one portion of the structure as a function of the relative velocity. For example, the third arrangement can generate the image using an optical frequency domain interferometric procedure, an optical coherence interferometric procedure and/or an ultrasound procedure. At least a portion of the third arrangement is provided in a catheter.

In yet another exemplary embodiment of the present disclosure, the first arrangement can include a portion having a section which is structured to reflect at least one of the first and/or second transmitted radiations and at least partially to allow to pass therethrough the other one of the first and/or second transmitted radiations based on respective wavelengths of the first and second transmitted radiations. For example, the reflected radiation and the pass through radiation can be provided at the predetermined angle. Further, the first arrangement can be structured to collimate and/or focus the first transmitted radiation and/or the second transmitted radiation. In addition, the first and second axes can impact the structure at positive and negative angles, respectively, with respect to an axis perpendicular to a surface of the structure. The second arrangement can be further configured to distinguish between a relative motion between the structure and the first arrangement in two dimensions based on the first and second returned radiations.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWING(S)

Further objects, features and advantages of the present invention will become apparent from the following detailed description taken in conjunction with the accompanying figures showing illustrative embodiments of the present invention, in which.

Figure 2:
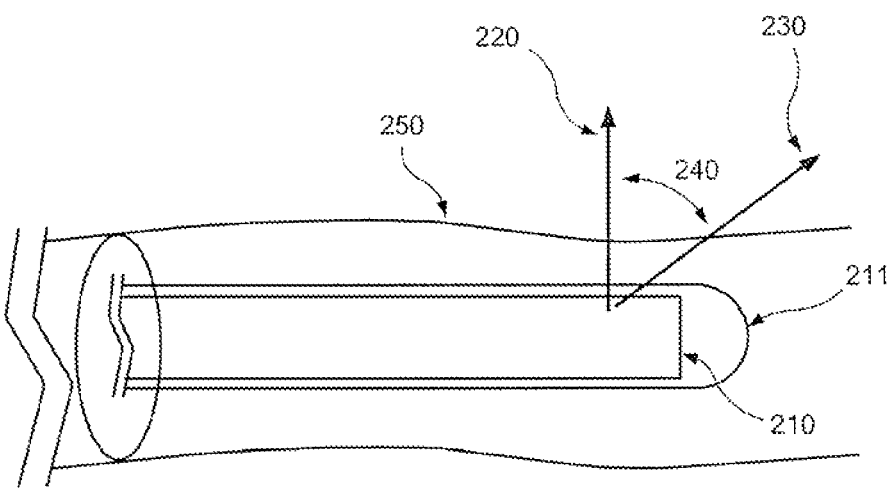
FIG. 2 is a side cross-sectional view of a catheter according to an exemplary embodiment of the present invention for tracking relative distance and/or motion between a conduit within the catheter and a lumen.
Figure 5:
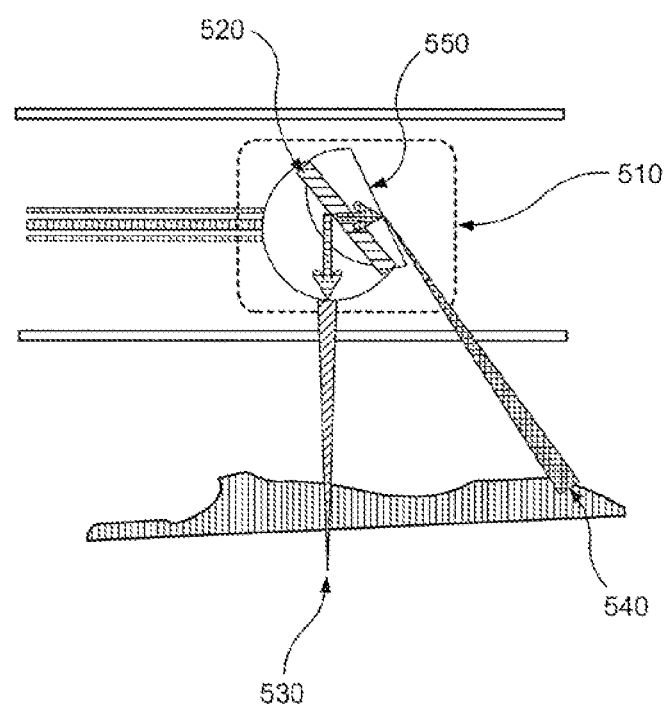
Figure 6:
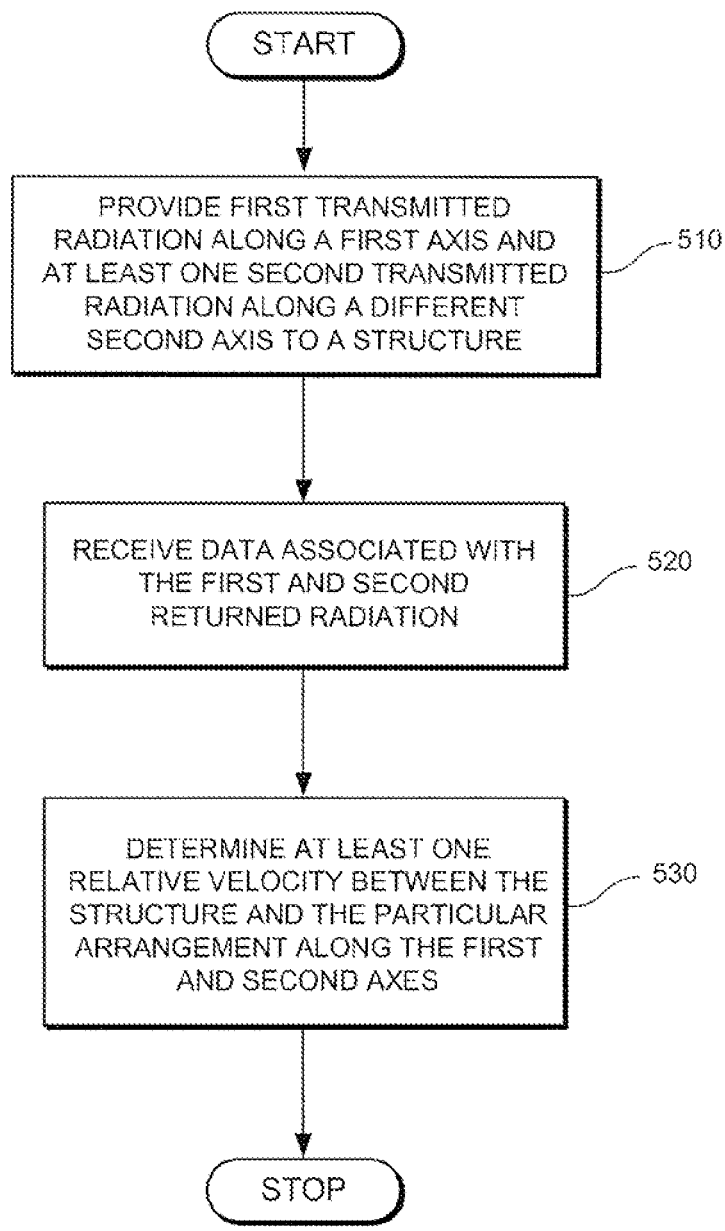

FIG. 5 is a side cross-sectional view of an exemplary embodiment of certain components of the exemplary catheter shown in FIG. 2, which can be used for monitoring the relative motion and/or velocity between the catheter conduit and the target; and FIG. 6 is a flow diagram of an exemplary embodiment of a method according to the present disclosure for determining at least one characteristic of a structure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

Figure 1:
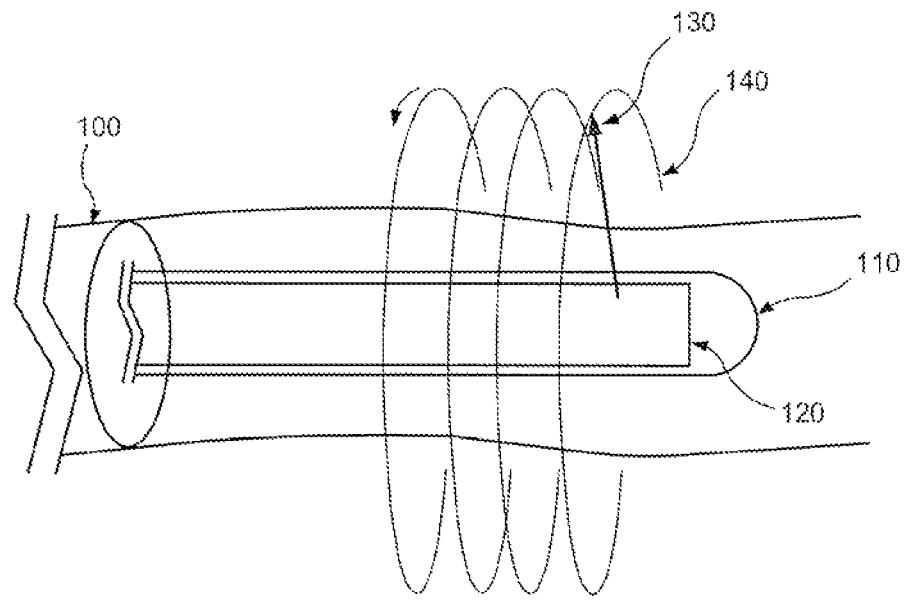
FIG. 1 is a side cross-sectional view of a catheter which utilizes a conventional scanning technique for a three-dimensional imaging.

FIG. 1 shows a side cross-sectional view of an example of a conventional catheter using which monitoring of relative spatial locations or motions between two objects would likely be beneficial. Turning to FIG. 1, when delivering light, e.g. for imaging or therapy, through such catheter or an endoscope to the lumen 100 of an internal organ 100, it is possible to utilize a catheter comprising an external sheath 110 and an internal conduit 120 that can be rotated and/or translated within the sheath. When the conduit 120 is configured to deliver light along a particular axis 130, the exposure of light to a predetermined portion of the lumen 100 can be achieved by rotating and longitudinally scanning the conduit while also controlling the irradiance delivered by the conduit. For example, this strategy can be utilized for imaging the lumen 100. In such cases, it can be important that the resulting helical scan pattern 140 exposes the entire surface area of the lumen 100.

Typically, the sheath may be held fixed with respect to the lumen 100, and the location and orientation of the conduit can be remotely monitored with respect to the sheath. In this manner, the scan pattern of the light on the lumen 100 can be controlled. However, in instances when the relative location or motion of the sheath with respect to the lumen may not be controlled, the accuracy of the scan pattern can no longer be assured. This can be due to, for example, from respiration, peristalsis, cardiac function, or other sources of motion. Although such representative example of delivering light to the lumen of an internal biological organ can instructive for understanding a context of the exemplary embodiments of the present disclosure, it by no means represents the only application for which monitoring of the relative spatial location or motion between two objects would be beneficial.

FIG. 2 shows a side cross-sectional view of a catheter according to an exemplary embodiment of the present invention for tracking relative distance and/or motion between a conduit within the catheter and a lumen. According to such exemplary embodiment as illustrated in FIG. 2, the exemplary catheter 250 can be provided which can be suitable for imaging internal biological organs. Such exemplary catheter 250 can be structured or configured to include an internal conduit 210, which can be provided within an external and at least partially transparent sheath 211. The conduit can be configured or designed to emit electromagnetic radiation (e.g., light) or ultrasound radiation along two distinct axes 220 and 230 in such a way that a relative orientation between the two axes 220, 230 can be quantified by a relative angle 240.

When reflected or scattered radiation is returned along each of the axes 220, 230, such returned radiation can be collected by the conduit 210, and conveyed proximally within the catheter to an attached or coupled receiver and/or a processing arrangement (e.g., which can include a processor). Through the measurement of the reflected and/or scattered radiation, the magnitude of the relative velocity and/or the relative distance between the conduit 210 and the lumen along the respective axis 220, 230 can be determined. Further, since the relative angle between the two axes 220, 230 can be known and/or determined, comparing the velocity magnitude measurements along each axis can further provide the direction of the relative velocity.

In certain exemplary embodiments of the present disclosure, measurements of the relative distance and or velocity along certain specified axes 220, 230 between the conduit 210 and the lumen may be used to correct for motion arising from, for example, peristalsis, cardiac function, respiration, or other sources of motion. Such exemplary measurements can be used, for example, to alter a scan pattern of the conduit 210 with respect to the sheath 211 so that a uniform, pre-determined scan pattern can result between the conduit and the lumen 100. Certain exemplary methods and/or techniques known in the field of medical imaging can be used for controlling the scan patterns of conduits within catheters, including, e.g., external motors, located at the proximal catheter end and attached to the conduit and sheath, internal motors located within the sheath for rotating and or translating the conduit with respect to the sheath, and miniature electromechanical, galvanometric, and/or magneto-mechanical actuators for rotating and or translating the conduit with respect to the sheath. Alternatively or in addition, such exemplary actuators can be used to control the orientation of the optical axes directly.

According to certain exemplary embodiments of the present disclosure, it is possible to apply methods of low-coherence interferometry to determine the distance between the conduit 210 and the lumen. Such exemplary measurements can include coherence-domain ranging, frequency-domain ranging, and time-domain ranging. In such exemplary embodiments of the present disclosure, further processing of distance measurements can be applied to determine a relative velocity between the conduit 210 and the lumen. For example, the distance measurements can be monitored over time to provide a derivative which can be proportional to the relative velocity.

According to further exemplary embodiments of the present disclosure, it is possible to utilize measurements that can provide a magnitude of the relative velocity along the specified axes 220, 230. Such exemplary measurements can be integrated to provide the relative distances and can include, but are certainly not limited to, exemplary measurements such as the rate of temporal decorrelation of a speckle pattern or the Doppler frequency shift imparted on the reflected or scattered light, etc. In the presence of relative motion between a conduit and a lumen, the radiation (e.g., light) reflected, for example, along the axes 220, 230 can be frequency shifted and/or Doppler shifted by an amount that can depend on the relative velocity, the incidence angle θ, and/or the tracking wavelength λ:

$$f_D = \frac{2}{\lambda}(v_r \cos\theta + v_z \sin\theta), \tag{1}$$

where $v_r$ and $v_z$ are, respectively, the relative radial and longitudinal velocities of the lumen with respect to the conduit. Because the exemplary radiation provided via the axes 220, 230 impact and/or illuminate the lumen at different angles, such exemplary beams and/or radiations can experience different Doppler shifts for the same velocities:

$$\begin{pmatrix} f_1 \\ f_2 \end{pmatrix} = \frac{2}{\lambda} \begin{pmatrix} \cos\theta_1 & \sin\theta_1 \\ \cos\theta_2 & \sin\theta_2 \end{pmatrix} \begin{pmatrix} v_r \\ v_z \end{pmatrix}. \tag{2}$$

For example, if the first and second exemplary beams and/or radiations impact and/or illuminate the surface of the lumen at positive and negative angles, respectively, with respect to an axis perpendicular to the surface of the lumen, then the first and second exemplary beams and/or radiations can be used to distinguish relative motion between the lumen and the catheter in the longitudinal and radial directions. In certain exemplary embodiments employing such exemplary geometry, motion of the lumen in the +z direction (e., along the axis of the lumen) relative to the conduit 210 can cause the first exemplary beam and/or radiation to shift up in frequency, while simultaneously causing the second exemplary beam and/or radiation to shift down in frequency. For example, motion of the lumen in the −z direction can cause the first exemplary beam and/or radiation to shift down in frequency, while simultaneously causing the second exemplary beam and/or radiation to shift up in frequency.

At the same time, e.g., motion of the lumen in the +r direction (e.g., of the lumen towards the catheter) can cause both beams and/or radiations to shift up in frequency; whereas, motion in the −r direction can cause both beams and/or radiations to shift down in frequency. Thus, relative motion in the two dimensions can be resolved because the beams and/or radiations experience oppositely directed Doppler shifts for motion along a first dimension and Doppler shifts in the same direction for motion along the second dimension. Those having ordinary skill in the art will certainly understand that adding a third beam and/or radiation at an appropriate angle can facilitate a resolve relative motion in a third dimension (and/or improve the accuracy of measurements in the first and second dimensions).

Those having ordinary skill in the art will further certainly understand that a beam transmitted along an axis normal to the surface of the lumen would likely not experience a Doppler shift for relative longitudinal motion. Motion in the two directions can still be resolved according to certain exemplary embodiments employing such a geometry. This is because, for example, the other beam and/or radiation can still experience a Doppler shift for longitudinal motion. Thus, the radial motion can cause both beams and/or radiations to experience a Doppler shift; whereas, longitudinal motion can cause only one beam and/or radiation to experience a Doppler shift. This difference can facilitate the ability to distinguish the two directions of motion.

Equation (2) illustrates that the exemplary frequency shift measurements along the two axes 220, 230 can form a basis set (e.g., not an orthonormal set) for resolving the two relative velocity components of the lumen with respect to the conduit. Inverting the matrix in Eq. (2) can provide the relative velocities in terms of the incidence angles and the measured Doppler shifts:

$$\begin{pmatrix} v_r \\ v_z \end{pmatrix} = \frac{\lambda}{2\sin(\theta_2 - \theta_1)} \begin{pmatrix} \sin\theta_2 & -\sin\theta_1 \\ \cos\theta_2 & \cos\theta_1 \end{pmatrix} \begin{pmatrix} f_1 \\ f_2 \end{pmatrix}. \quad (3)$$

In certain exemplary applications, it is possible to configure or provide the optical axes 220, 230 such that one of the axes 220, 230 can be approximately normal to the lumen, so that relative velocity or distance measurements along this axis represent radial relative motion. Further, it is possible to configure or provide the optical axes 220, 230 such that the relative angle 240 between them is greater than, e.g., approximately 45 degrees but less than, e.g., approximately 90 degrees. Exemplary measurements of Doppler frequency shifts can be facilitated by mixing light returning along the optical axes with light from a local oscillator, or heterodyne reference, which can be coherent with the radiation (e.g., the light) emitted from the conduit, along the axes 220, 230.

Figure 3:
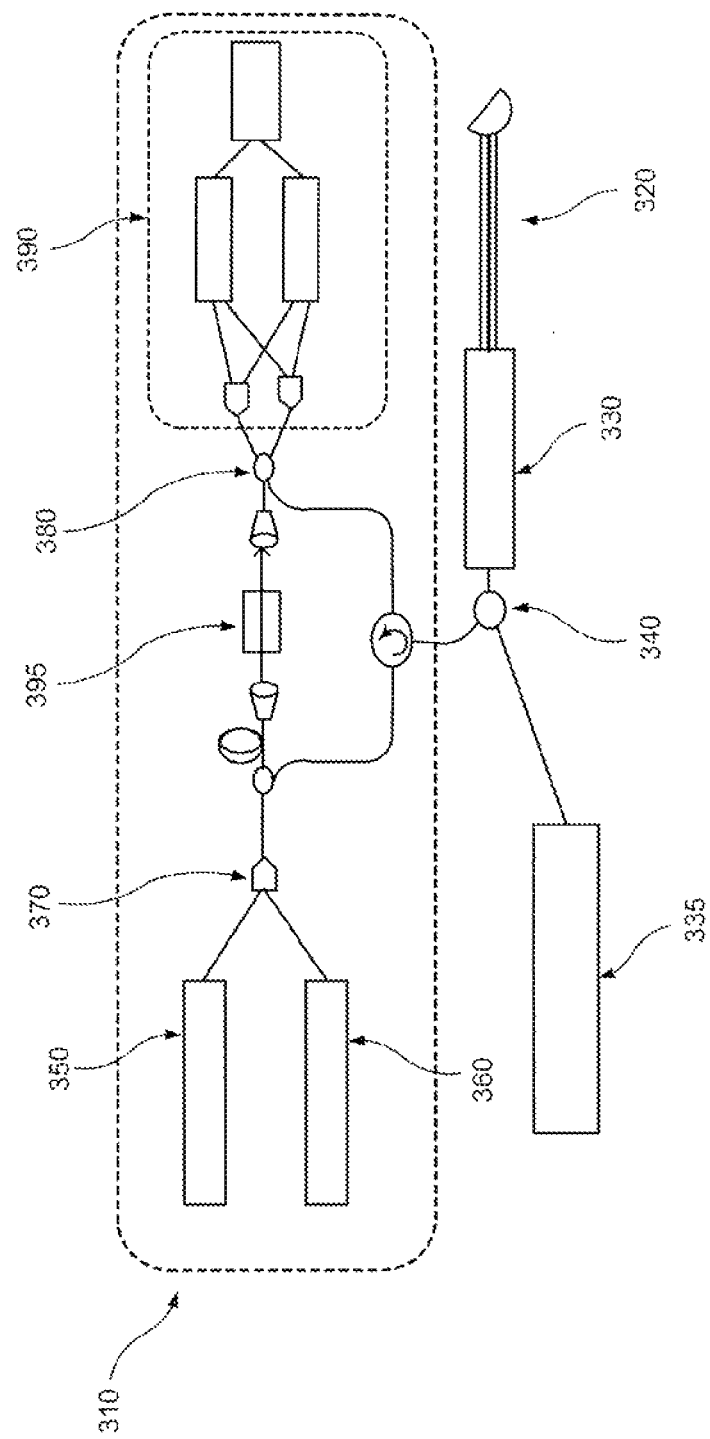
FIG. 3 is a diagram of an exemplary embodiment of a system/apparatus according to the present disclosure for processing signals returned from the exemplary catheter shown in FIG. 2.

FIG. 3 illustrates an exemplary embodiment of a system/apparatus according to the present disclosure for processing signals returned from the exemplary catheter shown in FIG. 2. For example, a beam director 340, for example, a wavelength division multiplexer, can be provided at a proximal end of a conduit 320 that can transmit a returned radiation (e.g., light) so that it can be combined with the radiation (e.g., light) from a local oscillator using a coupler 380. Radiation (e.g., light) returned along each axis can be further separated and/or detected by separate receivers 390. The detected signal associated with radiation (e.g., light) returning along one of the first and second axes 220 can be subject to the following exemplary approximation, $$I(t) \approx I_{LO} + \sqrt{I_{LO}I_1} \cos[2\pi(f_{LO}-f_1)t], \quad (4)$$

where $I_{LO}$ is the local oscillator intensity, $f_{LO}$ is the local oscillator frequency, and $I_1$ is the intensity of the returned light corresponding to axis 1. An exemplary knowledge and/or determination of the frequency of the local oscillator can therefore be utilized to determine the frequency of the returned light, and using Equation 3, to determine the corresponding relative velocity.

For example, a heterodyne reference beam can serve, e.g., two purposes: i) amplifying the signal, and/or ii) making it possible to distinguish the direction of motion. For example, if $f_{LO}=0$, approximately equal but oppositely directed velocities may produce signals that oscillate at the same frequency. When $f_{LO}>f_1, f_2$, approximately equal but oppositely directed velocities may cause the detected signal to shift away from the local oscillator frequency in opposite directions, removing this ambiguity.

The signal-to-noise ratio (SNR) of the detected signal can limit the precision of the frequency measurement, which, in turn, limits the precision of the velocity estimate. In addition, any difference between the actual angles of incidence from the assumed angles of incidence can result in errors in the velocity estimate. Because the tracking beam and/or radiation can refract through the facet over a small range of angles, however, the Doppler shift of the refracted beam and/or radiation can span a small range of frequencies centered at the nominal Doppler frequency, $f_2$. If the angle of incidence changes, the angular spread can change as well, likely causing, e.g., the peak at $f_2$ to become broader or narrower. Similarly, angular spread in the reflected beam and/or radiation can affect the shape of the peak at $f_1$.

Alternatively or in addition, according to a further exemplary embodiment of the present disclosure, another optical element cantilevered from the probe tip or suspended in the sheath can be used to reflect and possibly collimate or focus the refracted beam and/or radiation towards the spot being imaged. Collimating the beam and/or radiation can sharpen the Doppler-shifted peak, as would likely focusing, provided that the angular spread of the focused beam and/or radiation is smaller the angular spread of the refracted beam and/or radiation alone.

In semi-rigid lumens, projecting both tracking beams and/or radiations onto the same spot can also improve the accuracy of velocity estimation as long as the interbeam angle (e.g., $\theta_1-\theta_2$) can remain large. In a semi-rigid vessel, e.g., different parts of the vessel can move at different velocities, e.g., likely degrading the velocity estimate made by measuring the Doppler shifts of beams and/or radiations illuminating different spots. Bringing the tracking beam/radiation spots close together while maintaining a large interbeam angle can reduce or eliminate such problem, while possibly preserving tolerance to angular misalignment.

In further exemplary embodiments of the present disclosure, additional optical axes (>2) can be utilized and reflected or scattered light corresponding to each axis may be processed to yield relative distance and or velocity using the exemplary methods and procedures described above. This additional information can be useful for decreasing sensitivity of measurements to noise or to improve the accuracy with which the relative distance, velocity or direction of velocity can be determined.

Further exemplary embodiments according to the present disclosure can be directed to techniques, apparatus and computer accessible medium that facilitate a unique identification of each optical axis. Such exemplary techniques, apparatus and computer-accessible medium can include, e.g., wavelength division multiplexing, time division multiplexing and frequency division multiplexing. For example, turning back to FIG. 3, this figures illustrates a wavelength-division multiplexing instrument 310 for determining the relative distance and or velocity of a catheter conduit 320 with respect to a lumen. For example, actuators 330 can be located at the proximal end of the catheter to control the rotation and or longitudinal location of the distal conduit end.

A wavelength division multiplexer 340 can be used to deliver radiation (e.g., light) from the instrument 310 into an imaging system, which can comprise a console 335, the actuators 330 and a catheter conduit 320. The exemplary instrument 310 can include multiple independent light sources 350 and 360, which can be combined into a single optical path using a wavelength division multiplexer 370. The radiation (e.g., light) sources can be uniquely identified by their wavelength or by frequency or amplitude modulation patterns incorporated into their emission. The single optical path can be subsequently divided into two paths, one path which can be in communication with the imaging system and another path representing a reference path.

The use of modulators 395, such as but not limited to acousto-optic, electro-optic or magneto-optic, can improve the sensitivity of detection of the desired relative velocity and or relative distance parameters. For example, radiation (e.g., light) from each path, including radiation/light returning from the lumen, can be recombined using the coupler 380, and directed to the receiver 390. The receiver 90 can be configured to separate the optical signals into paths corresponding to each independent light source and to measure, for example, the Doppler frequency shift or delay corresponding to the relative distance and or motion of the catheter conduit with respect to the lumen. The incorporation of the modulator or frequency shifter 395 into the reference path can be useful, e.g., for overcoming noise in the system.

Figure 4:
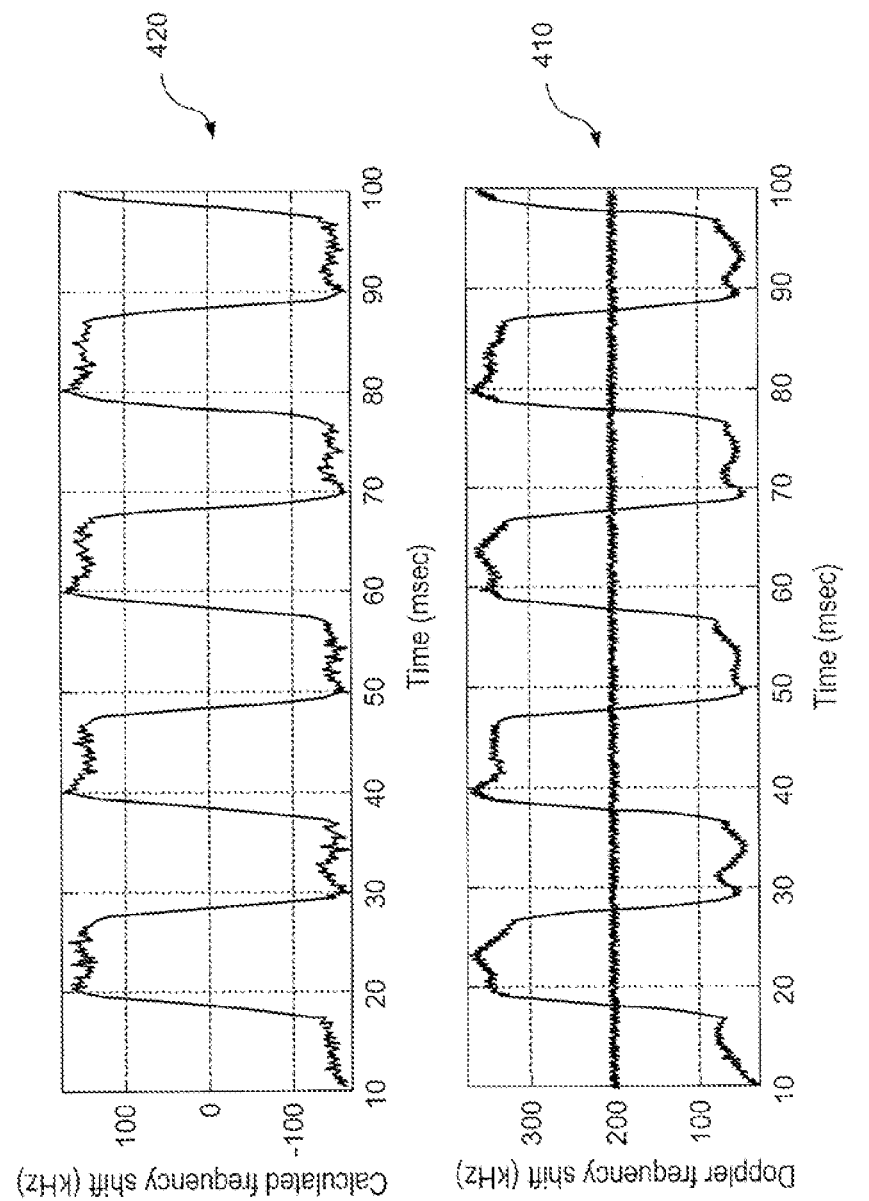
FIG. 4 is a pair of graphs illustrating plots of data acquired by the exemplary system/apparatus shown in FIG. 3 for tracking the relative motion between a catheter conduit and a target (e.g., a lumen)

FIG. 4 shows a pair of graphs illustrating plots of data acquired by the exemplary system/apparatus shown in FIG. 3 for tracking the relative motion between a catheter conduit and a target (e.g., a lumen). For example, a trace 410 represents data acquired by the exemplary embodiment of FIG. 3, and can display a time varying Doppler frequency, which can be proportional to the actual relative velocity between a conduit and a sample. A trace 420 depicts a theoretical Doppler shift, corresponding to the actual relative motion.

The combination of the exemplary embodiments of the present disclosure with techniques, such as ultrasonic imaging or therapy and optical imaging or therapy, be readily achieved as should be understood by those having ordinary skill in the art after reviewing the present disclosure. For example, in the exemplary embodiments, the axes 220, 230 that can be utilized to determine relative distance and or velocity can be delivered in a spatially co-registered orientation with respect to the imaging or therapy axes. Further, one of the axes 220, 230 can be one of the axes used for imaging or therapy. In this example, the axis 220 can represent both an imaging or therapy axis and an axis for determining relative distance and or velocity. For ultrasound and optical imaging techniques, this exemplary combination can be achieved.

Further exemplary embodiments of the present disclosure can be further configured to control the relative orientation of the axes 220, 230 along which relative distances or velocities may be determined. For example, as shown in one exemplary embodiment configured for registering the relative distance and or motion in conjunction with optical imaging as illustrated in FIG. 5, an optical transducer 510 can be configured to direct two or more optical axes in predetermined directions. An exemplary transducer 510 can include reflective, refractive and or diffractive surfaces. For example, one such exemplary dichroic reflective surface 520 can be configured to reflect radiation (e.g., light) of specific wavelengths and transmit radiation (e.g., light) having different wavelengths.

Dichroic filters can be constructed using dielectric coatings or facets at discontinuities of refractive indices, as is well known in the art. One exemplary configuration can include another exemplary dichroic surface 520 for which radiation (e.g., light) having wavelengths lower than a predetermined value may be reflected, and radiation (e.g., light) having a longer wavelength may be transmitted. This exemplary configuration can be utilized to produce two distinct axes 530, 540. Further, the optical transducer 510 can be configured to include a refractive facet 550 which can be distal to the dichroic surface such that radiation (e.g., light) transmitted through a facet 550 follows an axis 540 that is inclined in a forward direction. Alternatively or in addition, the facet 550 can be followed by a reflective surface, such as, e.g., a mirror, oriented to provide any directional orientation of axis 540. An optical transducer 510 can further be configured to focus light along one or more of the axes to a predetermined focal plane. In this exemplary embodiment, the axis 530 can include more than one optical beam. For example, the axis 530 can include light used for determining relative distance and or velocity according to the exemplary embodiment of the present disclosure, as well as light used for imaging or treating the biological lumen.

In further exemplary embodiments of the present disclosure, the exemplary techniques, apparatus and methods of the present disclosure can be implemented using other forms of propagating energy rather than light. Such exemplary embodiments can utilize, e.g., ultrasonic energy to determine the relative distance or the relative velocity between a transducer and lumen. FIG. 6 shows flow diagram of an exemplary embodiment of a method according to the present invention determining at least one characteristic of a structure which can be executed by a processing arrangement, and memorialized, e.g., using software stored or provided on a computer-accessible medium (e.g., hard drive, floppy disk, memory device such as a memory stick of other memory or storage device, or ac combination of one or more thereof).

In particular, as shown in FIG. 6, at least one first transmitted radiation can be provided along a first axis and at least one second transmitted radiation can be provided along a second axis using a particular arrangement (procedure 510). For example, the first and second transmitted radiations can impact the structure and generate at respective first and second returned radiation, and the first and second axis can be provided at a predetermined angle with respect with one another which is greater than 0. Further, as provided in procedure 520, data associated with the first and second returned radiations can be received. In addition, at least one relative velocity between the structure and the particular arrangement along the first and second axes can be determined (procedure 530).

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with and/or implement any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus for determining at least one characteristic of a structure, comprising:
    at least one transceiver first arrangement which is structured to provide at least one first transmitted radiation along a first axis and at least one second transmitted radiation along a second axis, wherein the first and second transmitted radiations impact the structure and generate respective first and second returned radiation, and wherein the first and second axes are provided at a predetermined angle with respect with one another which is greater than 0;
    at least one computer second arrangement which is configured to receive data associated with the first and second returned radiation, and determine at least one relative velocity between the structure and the at least one first arrangement; and
    at least one imaging third arrangement which is configured to generate at least one image of at least one portion of the structure as a function of the at least one relative velocity.

2. The apparatus according to claim 1, wherein the first and second transmitted radiations are electro-magnetic radiations.

3. The apparatus according to claim 1, wherein the first and second transmitted radiations have different wavelengths.

4. The apparatus according to claim 1, wherein the data corresponds to a Doppler shift between the first and second transmitted radiations and the first and second returned radiations.

5. The apparatus according to claim 1, wherein the data corresponds to a time rate of change of a distance between the apparatus and the structure along the first and second axes.

6. The apparatus according to claim 1, wherein the at least one first arrangement extends along a longitudinal axis, and wherein a first velocity along the first axis and a second velocity along the second axis is used to determine a further relative velocity between the apparatus and the structure at least approximately along the longitudinal axis.

7. The apparatus according to claim 6, wherein at least one of a position or a rotation of the apparatus is determined based on the further relative velocity.

8. The apparatus according to claim 1, wherein the at least one third arrangement generates the at least one image using an optical frequency domain interferometry procedure.

9. The apparatus according to claim 1, wherein the at least one third arrangement generates the at least one image using an optical coherence interferometry procedure.

10. The apparatus according to claim 1, wherein the at least one third arrangement generates the at least one image using an ultrasound procedure.

11. The apparatus according to claim 1, wherein at least a portion of the at least one third arrangement is provided in a catheter.

12. A method for determining at least one characteristic of a structure, comprising:
    with a transceiver arrangement, providing at least one first transmitted radiation along a first axis and at least one second transmitted radiation along a second axis, wherein the first and second transmitted radiations impact the structure and generate respective first and second returned radiation, and wherein the first and second axes are provided at a predetermined angle with respect with one another which is greater than 0;
    with at least one computer processor arrangement, receiving data associated with the first and second returned radiation, and determining at least one relative velocity between the structure and the transceiver arrangement; and
    generating at least one image of at least one portion of the structure as a function of the at least one relative velocity.

* * * * *